(12) United States Patent
Watanabe

(10) Patent No.: US 9,384,650 B2
(45) Date of Patent: Jul. 5, 2016

(54) ORGANISM SAMPLE MEASUREMENT DEVICE AND ORGANISM SAMPLE MEASUREMENT SENSOR HOUSING DEVICE

(75) Inventor: Atsushi Watanabe, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 412 days.

(21) Appl. No.: 14/234,683

(22) PCT Filed: Jul. 27, 2012

(86) PCT No.: PCT/JP2012/004814
§ 371 (c)(1),
(2), (4) Date: Jan. 24, 2014

(87) PCT Pub. No.: WO2013/014944
PCT Pub. Date: Jan. 31, 2013

(65) Prior Publication Data
US 2014/0177671 A1 Jun. 26, 2014

(30) Foreign Application Priority Data
Jul. 27, 2011 (JP) ................. 2011-163978

(51) Int. Cl.
*G01N 33/487* (2006.01)
*G08B 21/18* (2006.01)
*G01N 27/28* (2006.01)
*G01N 27/416* (2006.01)

(52) U.S. Cl.
CPC ............... *G08B 21/18* (2013.01); *G01N 27/28* (2013.01); *G01N 27/416* (2013.01); *G01N 33/48778* (2013.01)

(58) Field of Classification Search
None
See application file for complete search history.

(56) References Cited

U.S. PATENT DOCUMENTS

| 7,875,243 B2 | 1/2011 | Rush et al. |
| 7,998,407 B2 | 8/2011 | Wohland |
| 8,231,548 B2 | 7/2012 | Hoenes |
| 8,506,505 B2 | 8/2013 | Hoenes |

(Continued)

FOREIGN PATENT DOCUMENTS

| CN | 101754718 | 6/2010 |
| JP | 2001-281242 | 10/2001 |

(Continued)

OTHER PUBLICATIONS

Search report from E.P.O., mail date is Sep. 23, 2014.

(Continued)

*Primary Examiner* — Robert R Raevis
(74) *Attorney, Agent, or Firm* — Greenblum & Bernstein, P.L.C.

(57) ABSTRACT

An organism sample measurement device is capable of suppressing the degradation of the performance of an organism sample measurement sensor by notifying that the lid of a housing part housing the organism sample measurement sensor is open. In this organism sample measurement device (1), a measurement unit (21) measures organism information using the organism sample measurement sensor mounted in a sensor mounting part. A first detection switch (13) detects that the lid of a sensor bottle is open. A display unit (2) notifies the measurement result of the organism information measured by the measurement unit (21), and on the basis of the result of the detection by the first detection switch (13), displays error information indicating that the lid is open.

14 Claims, 18 Drawing Sheets

(56) References Cited

U.S. PATENT DOCUMENTS

| | | |
|---|---|---|
| 8,657,762 B2 | 2/2014 | Takashima et al. |
| 8,802,009 B2 | 8/2014 | Rush et al. |
| 2005/0143675 A1 | 6/2005 | Neel et al. |
| 2007/0212258 A1 | 9/2007 | Neel et al. |
| 2008/0145277 A1 | 6/2008 | Wohland |
| 2008/0190766 A1 | 8/2008 | Rush et al. |
| 2009/0182244 A1 | 7/2009 | Hoenes |
| 2010/0222703 A1 | 9/2010 | Takashima et al. |
| 2011/0097808 A1 | 4/2011 | Rush et al. |
| 2012/0271132 A1 | 10/2012 | Hoenes |

FOREIGN PATENT DOCUMENTS

| | | |
|---|---|---|
| JP | 2007-520699 | 7/2007 |
| JP | 2009-530608 | 8/2009 |
| JP | 2010-127786 | 6/2010 |
| WO | 2009/011137 | 1/2009 |

OTHER PUBLICATIONS

Search report from International Search Report in PCT/JP2012/004814, mail date is Aug. 28, 2012.

English translation of search report for China Office action, dated Aug. 27, 2014.

| HUMIDITY S / TEMPERATURE T | S≦10% | 10%<S≦30% | 30%<S≦50% | 50%<S≦70% | 70%<S |
|---|---|---|---|---|---|
| 0°C≦T≦10°C | 10 | 20 | 30 | 40 | 50 |
| 10°C<T≦20°C | 10 | 20 | 30 | 40 | 60 |
| 20°C<T≦30°C | 20 | 30 | 50 | 50 | 70 |
| 30°C<T≦40°C | 20 | 30 | 50 | 60 | 80 |
| 40°C<T | 20 | 30 | 50 | 70 | 90 |

FIG. 14

ORGANISM SAMPLE MEASUREMENT DEVICE AND ORGANISM SAMPLE MEASUREMENT SENSOR HOUSING DEVICE

TECHNICAL FIELD

The present invention relates to a biological sample measuring apparatus and a biological sample measuring sensor housing apparatus, which house a biological sample measuring sensor.

BACKGROUND ART

Conventionally, biological sample measuring apparatus are known which are composed of a sensor bottle that houses a biological sample measuring sensor, and a biological sample measuring apparatus main body to which the sensor bottle is installed (see, e.g., Patent Literatures 1 and 2). In Patent Literatures 1 and 2, a sensor bottle and a biological sample measuring apparatus are integrated, thereby making it possible to easily carry and handle the biological sample measuring sensor and the biological sample measuring apparatus.

In the biological sample measuring apparatuses disclosed in Patent Literatures 1 and 2, when measuring blood glucose levels, a closure of a sensor bottle is opened so that a biological sample measuring sensor housed in the sensor bottle is taken out. The biological sample measuring sensor thus taken out is installed to a sensor installment section of the biological sample measuring apparatus. Blood exuded out of skin punctured by an external puncture apparatus is spotted on the biological sample measuring sensor installed to the sensor installment section. Then, the biological sample measuring apparatus measures blood glucose levels.

The performance of the biological sample measuring sensor degrades under the influence of factors such as humidity and temperature. Therefore, a user has to close the closure of the sensor bottle after immediately taking out a biological sample measuring sensor.

CITATION LIST

Patent Literature

PTL 1
Japanese Unexamined Patent Application Publication (Translation of PCT Application) No. 2007-520699
PTL 2
Japanese Unexamined Patent Application Publication (Translation of PCT Application) No. 2009-530608

SUMMARY OF INVENTION

Technical Problem

However, in Patent Literatures 1 and 2, in the case where a user forgets to close the closure after opening the closure to take out a biological sample measuring sensor, or in the case where the closure is accidentally opened by an impact exerted on the sensor bottle, the user may not notice the fact that the closure is opened. This disadvantageously results in degradation in the performance of the biological sample measuring sensor housed in the sensor bottle.

An object of the present invention is to provide a biological sample measuring apparatus and a biological sample measuring sensor housing apparatus which can suppress degradation in the performance of the biological sample measuring sensor by appropriately notifying a user of the fact that a closure of a sensor bottle that houses a biological sample measuring sensor is open.

Solution to Problem

According to the present invention, there is provided a biological sample measuring apparatus to which a sensor bottle including a cylindrical housing section and a closure is installed, the housing section having an opening at one end thereof and being capable of housing a biological sample measuring sensor, the closure being configured to open and close the opening, the biological sample measuring apparatus including: a sensor installment section to which the biological sample measuring sensor is installed; a measurement section that measures biological information by using the biological sample measuring sensor installed to the sensor installment section; an open/close detection section that detects an open state of the closure; and a notifying section that notifies a measurement result of the biological information measured by the measurement section, and notifies error information indicating that the closure is open on the basis of a detection result detected by the open/close detection section.

According to the present invention, there is provided a biological sample measuring sensor housing apparatus to which a sensor bottle including a cylindrical housing section and a closure is installed, the housing section having an opening at one end thereof and being capable of housing a biological sample measuring sensor, the closure being configured to open and close the opening, the biological sample measuring sensor housing apparatus including: a detection section that detects an open state of the closure; and a notifying section that notifies error information indicating that the closure is open on the basis of a detection result detected by the detection section.

Advantageous Effects of Invention

According to the present invention, by appropriately notifying a user of the fact that the closure of the sensor bottle that houses the biological sample measuring sensor is open, possible degradation in the performance of the biological sample measuring sensor can be prevented.

BRIEF DESCRIPTION OF DRAWINGS

FIG. 14 is an exposure coefficient table according to Embodiment 2 of the present invention;

DESCRIPTION OF EMBODIMENTS

Figure 1:
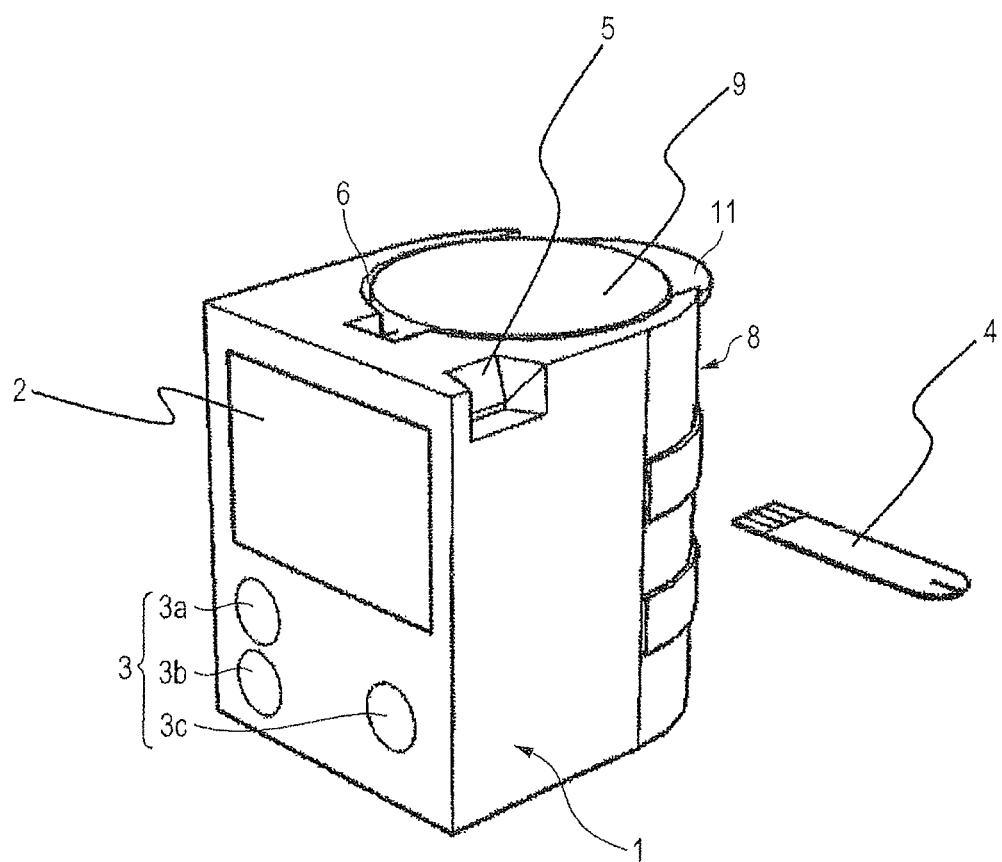
FIG. 1 is a front perspective view of a biological sample measuring apparatus in which a sensor bottle is installed according to Embodiment 1 of the present invention.
Figure 2:
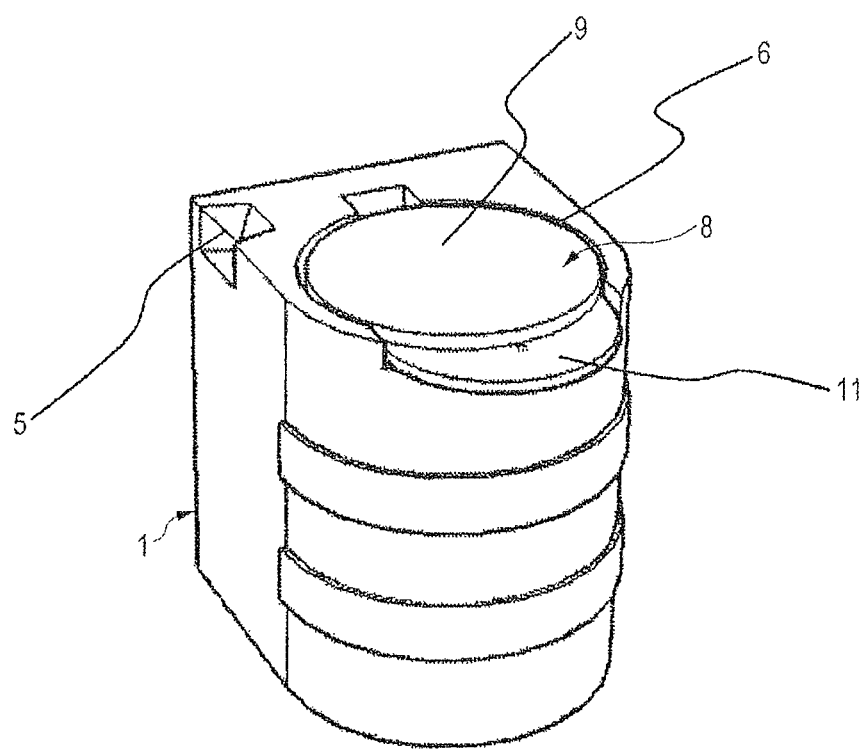
FIG. 2 is a rear perspective view of the biological sample measuring apparatus in which the sensor bottle whose closure is in a closed state is installed according to Embodiment 1 of the present invention.
Figure 3:
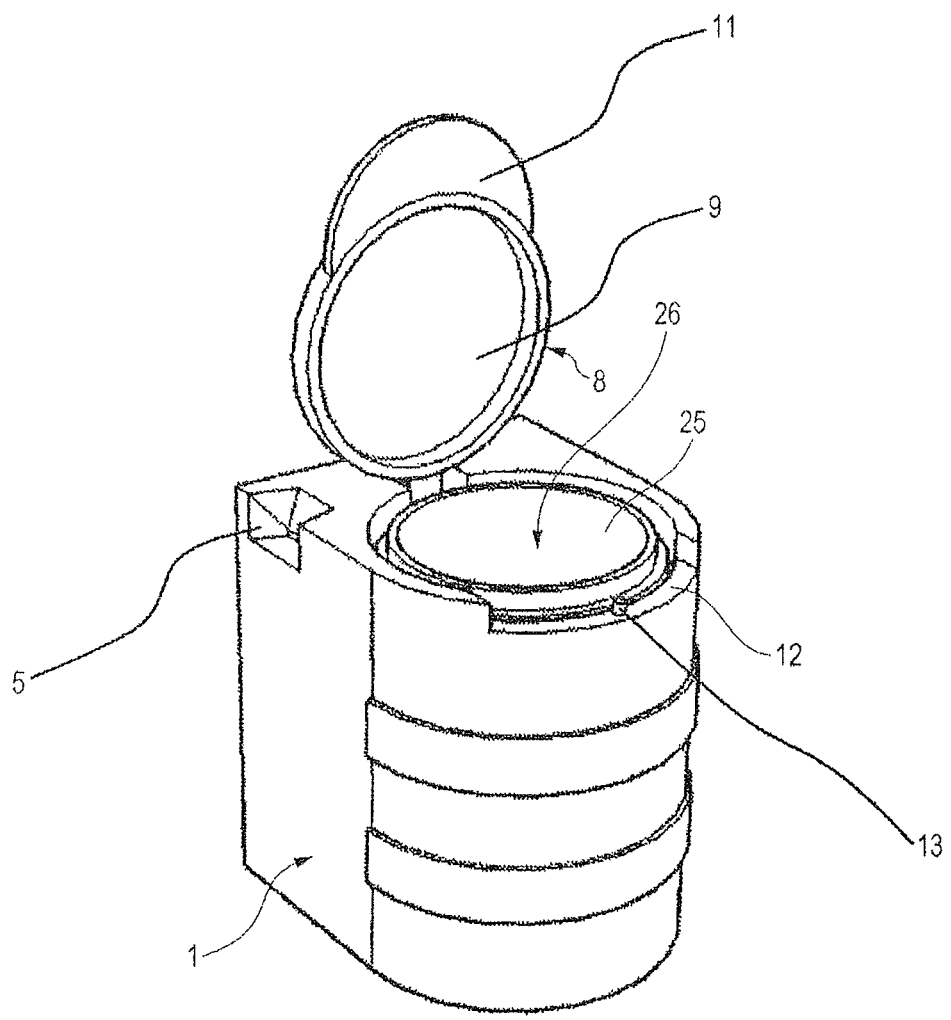
FIG. 3 is a rear perspective view of the biological sample measuring apparatus in which the sensor bottle whose closure is in an open state is installed according to Embodiment 1 of the present invention.

In the following, embodiments of the present invention will be described in detail with reference to the accompanying drawings.

Embodiment 1

<Mechanical Configuration of Biological Sample Measuring Apparatus>

A mechanical configuration of biological sample measuring apparatus 1 according to Embodiment 1 of the present invention will be described with reference to FIG. 1 to FIG. 5. It is to be noted in FIG. 1 that biological sample measuring sensor 4 and sensor bottle 8 are also illustrated together with biological sample measuring apparatus 1.

Biological sample measuring apparatus 1 mainly includes display section 2, operation section 3, sensor installment section 5, bottle installment section 6, recess 12, first detection switch 13, second detection switch 17 (bottle detection switch), and third detection switch 18 (bottle detection switch).

Biological sample measuring apparatus 1 has a cuboid form. Biological sample measuring sensor 4 is installed to biological sample measuring apparatus 1, and biological information is acquired from the installed biological sample measuring sensor 4. Here, the biological information is a blood glucose level, for example.

Display section 2, which serves as a notifying section, is provided on the front side of biological sample measuring apparatus 1. Display section 2 displays a measurement result of biological information, error information indicating that closure 9 is open, and an installment state of sensor bottle 8. Here, display section 2 can display the information in the following manner: Specifically, display section 2 can display the measurement result of biological information and error information at the same time on a single screen; display section 2 can display the measurement result of biological information first, and then error information; display section 2 can display error information first, and then the measurement result of biological information; or display section 2 can alternately display the measurement result of biological information and error information. Further, display section 2 can display error information at a desired timing. Display section 2 has a liquid crystal display or an organic EL display, for example.

Operation section 3 includes first operation section 3a, second operation section 3b, and third operation section 3c. Operation section 3 is operated to switch a display on display section 2, and to start a measurement for acquiring biological information, for example. It is to be noted that the number of operation section 3 is not limited to three.

Sensor installment section 5 is provided at an upper end portion of a side surface of biological sample measuring apparatus 1. Biological sample measuring sensor 4 is inserted and installed to sensor installment section 5 in order to acquire biological information. Sensor installment section 5 is provided with a plurality of terminals not illustrated which connect with biological sample measuring sensor 4.

Bottle installment section 6 is provided at an upper end portion thereof with upper opening portion 7. Bottle installment section 6 has a bottomed cylinder form. Sensor bottle 8 is housed in bottle installment section 6. Sensor bottle 8 is inserted from the upper opening portion 7 when it is installed to bottle installment section 6.

Recess 12 is provided at an upper end portion of the back side of biological sample measuring apparatus 1. Recess 12 is provided with first detection switch 13 (see FIG. 5).

Figure 4:
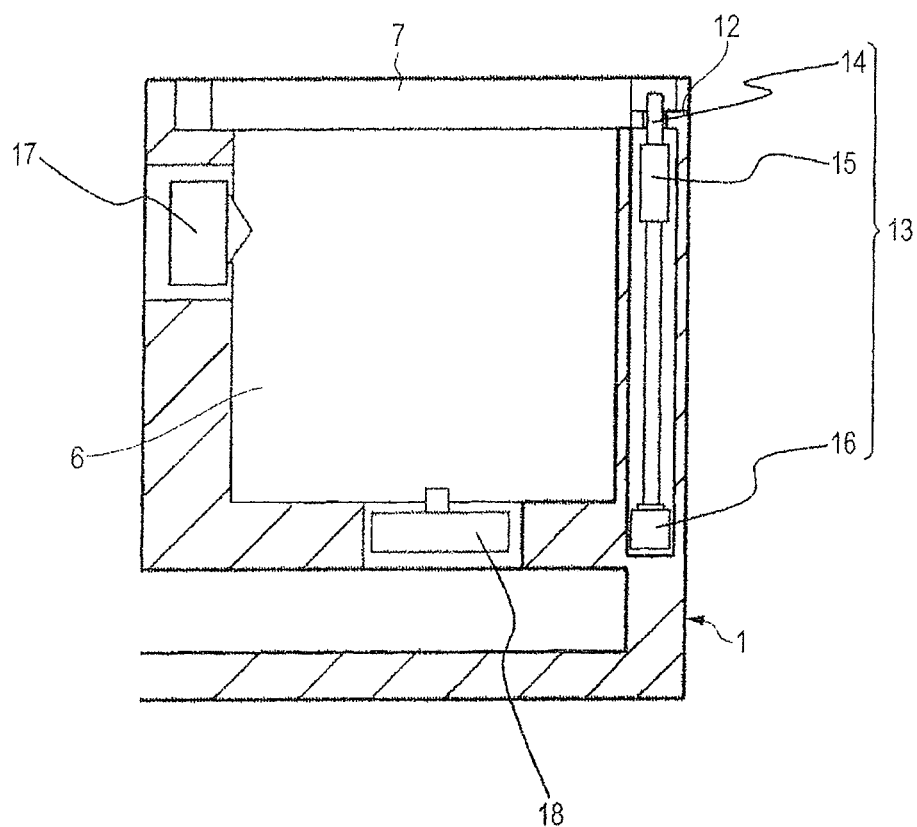
FIG. 4 is a sectional view illustrating a main part of the biological sample measuring apparatus according to Embodiment 1 of the present invention.
Figure 5:
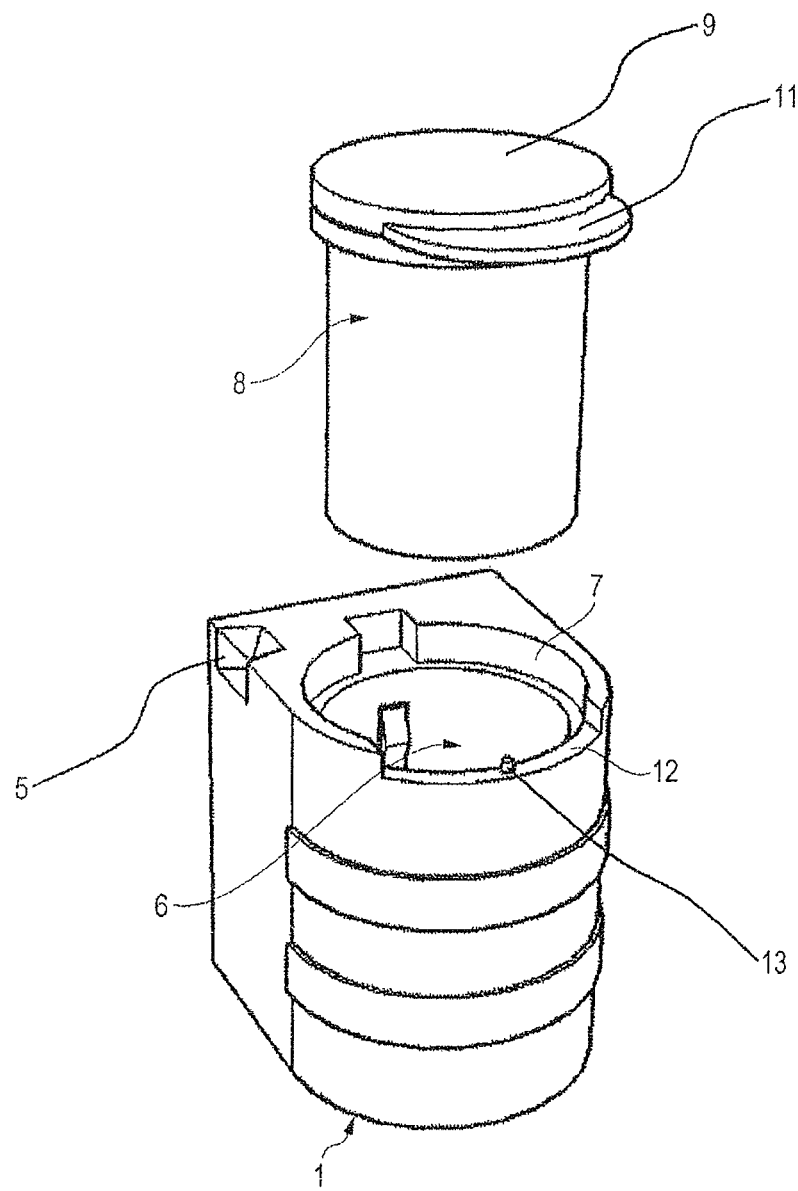
FIG. 5 is a rear perspective view of the sensor bottle and the biological sample measuring apparatus before the sensor bottle is installed thereto according to Embodiment 1 of the present invention.

First detection switch 13, which serves as an open/close detection section, includes actuator section 14, spring 15, and switch 16 (see FIG. 4). Actuator section 14 is disposed at recess 12. Spring 15 is disposed below actuator section 14. Switch 16 is disposed below spring 15. In first detection switch 13, when actuator section 14 is pressed by closure 9, actuator section 14 and spring 15 move downward to press switch 16. Then, when first detection switch 13 in the abovementioned state is further pressed, only spring 15 is compressed, whereby excessive load is prevented from being exerted on switch 16. First detection switch 13 detects opening and closing of closure 9.

Second detection switch 17, which serves as an installment detection section, is provided on an internal surface of bottle installment section 6 or on a bottom surface of bottle installment section 6. Alternatively, second detection switch 17 may be provided on both of the internal surface and the bottom surface of bottle installment section 6 (see FIG. 4).

Second detection switch 17 determines whether sensor bottle 8 is installed to bottle installment section 6. Third detection switch 18 determines whether sensor bottle 8 is properly installed to bottle installment section 6.

<Configuration of Sensor Bottle>

A configuration of sensor bottle 8 according to Embodiment 1 of the present invention will be described with reference to FIG. 1 to FIG. 6.

Figure 6:
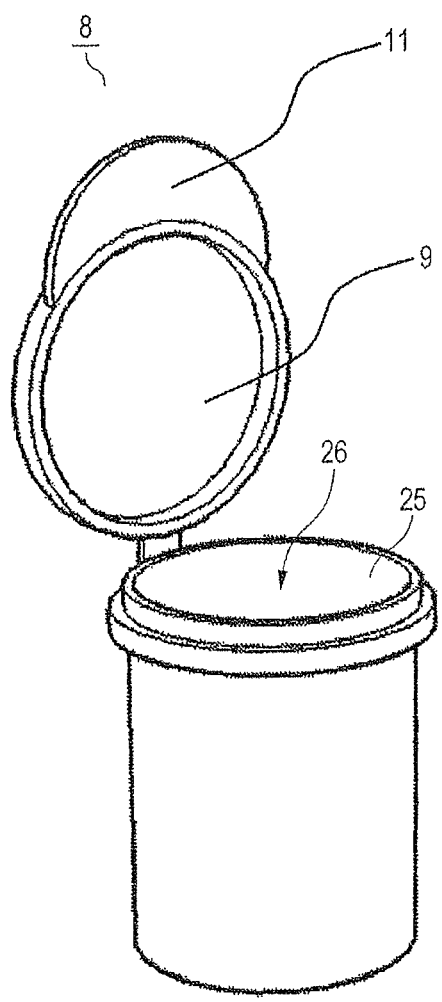
FIG. 6 is a perspective view of the sensor bottle according to Embodiment 1 of the present invention.

As illustrated in FIG. 6, sensor bottle 8 mainly includes closure 9, closure opening/closing section 11, and housing section 26.

Sensor bottle 8 has a cylindrical form (see FIG. 5 and FIG. 6), and is installed to biological sample measuring apparatus 1.

Closure 9 is provided in an openable manner on upper opening portion 25 provided at the upper end portion of housing section 26. In a closed state, closure 9 covers upper opening portion 25 (the state shown in FIG. 1 and FIG. 2). In other words, upper opening portion 25 is opened and closed with closure 9. In order to enhance the drying performance of a desiccant housed in housing section 26, closure 9 covers upper opening portion 25 except when necessary. Upper opening portion 25 is provided to take out biological sample measuring sensor 4 housed in housing section 26.

Closure opening/closing section 11 has a brim form, and is provided on closure 9. When closure 9 is in a closed state and sensor bottle 8 is installed in bottle installment section 6, closure opening/closing section 11 is provided at a position in which it faces recess 12 (see FIG. 3 and the like). Thus, when closure 9 is in a closed state, closure opening/closing section 11 presses down actuator section 14 of first detection switch 13.

Housing section 26 has a cylindrical form having an opening at one end thereof. Housing section 26 can house biological sample measuring sensor 4. Housing section 26 is provided with upper opening portion 25 for taking out biological sample measuring sensor 4. A desiccant (not illustrated) is housed in housing section 26.

<Configuration of Biological Sample Measuring Sensor>

Figure 7:
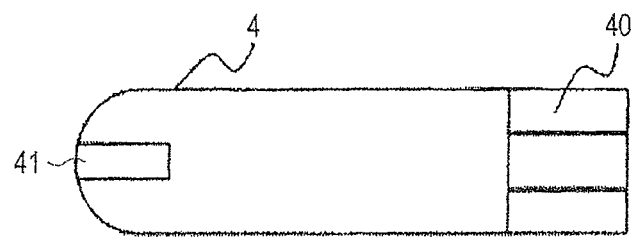
FIG. 7 is a plan view of a biological sample measuring sensor according to Embodiment 1 of the present invention.

A configuration of biological sample measuring sensor 4 according to Embodiment 1 of the present invention will be described with reference to FIG. 7.

Biological sample measuring sensor 4 mainly includes electrode section 40 and spot application section 41.

Biological sample measuring sensor 4 is housed in sensor bottle 8 in such a manner that electrode section 40 side thereof is located on the lower side of sensor bottle 8 and spot application section 41 side thereof is located on the upper side of sensor bottle 8.

When biological sample measuring sensor 4 is installed to sensor installment section 5, electrode section 40 is located in sensor installment section 5. Electrode section 40 detects a spot application of a biological sample on application section 41.

When biological sample measuring sensor 4 is installed to sensor installment section 5, electrode section 40 connects with a plurality of terminals (not illustrated) provided in sensor installment section 5. Then, via the terminals, electrode section 40 is electrically connected with measurement section 21 (see FIG. 8) and the like in biological sample measuring apparatus 1. With the above-mentioned configuration, biological sample measuring apparatus 1 detects an installment of biological sample measuring sensor 4, identifies the model of biological sample measuring sensor 4, detects a spot application of a biological sample, and measures the substrate concentration (for example, blood glucose level) of a biological sample, for example.

When biological sample measuring sensor 4 is installed to sensor installment section 5, spot application section 41 is located on the outside. A biological sample is spotted on spot application section 41. Here, the biological sample is blood, for example.

<Electrical Configuration of Biological Sample Measuring Apparatus>

An electrical configuration of biological sample measuring apparatus 1 according to Embodiment 1 of the present invention will be described with reference to FIG. 8.

Biological sample measuring apparatus 1 mainly includes display section 2, first operation section 3a, second operation section 3b, third operation section 3c, first detection switch 13, second detection switch 17, third detection switch 18, control section 19, sensor insertion detection section 20, measurement section 21, memory 22, buzzer 23, and sensor connection section 24. It is to be noted in FIG. 8 that the configurations same as those in FIG. 1 to FIG. 7 are denoted by the same reference numerals, and the descriptions thereof are omitted.

Control section 19 controls display section 2, first operation section 3a, second operation section 3b, third operation section 3c, and sensor connection section 24. Control section 19 acquires a measurement result measured by measurement section 21 and stores the result in memory 22. Control section 19 controls buzzer 23 to notify completion of measurement when a measurement performed by measurement section 21 is completed. Control section 19 controls display section 2 to display a result of the measurement performed by measurement section 21. Control section 19 acquires a result of detection performed at first detection switch 13, second detection switch 17, or third detection switch 18, and on the basis of the acquired result, controls display section 2 to display error information or an installment state of sensor bottle 8.

Sensor insertion detection section 20 detects biological sample measuring sensor 4 connected to sensor connection section 24.

Sensor insertion detection section 20 determines, in an electrical manner, whether electrode section 40 of biological sample measuring sensor 4 is connected to sensor connection section 24.

Measurement section 21 measures biological information by using biological sample measuring sensor 4. To be more specific, when a detection result indicating that biological sample measuring sensor 4 is connected to sensor connection section 24 is acquired from sensor connection section 24, measurement section 21 starts a measurement for acquiring biological information. Measurement section 21 outputs a measurement result to control section 19.

Memory 22 stores therein the measurement result input from control section 19.

Under the control of control section 19, buzzer 23 notifies completion of the measurement.

Sensor connection section 24 has sensor insertion detection section 20. When sensor insertion detection section 20 detects connection of biological sample measuring sensor 4, sensor connection section 24 outputs the detection result to measurement section 21. Sensor connection section 24 is provided in the above-mentioned sensor installment section 5. Sensor connection section 24 has a plurality of terminals (not illustrated) which electrically connect biological sample measuring sensor 4 and measurement section 21.

<Method of Acquiring Biological Information>

Figure 9:
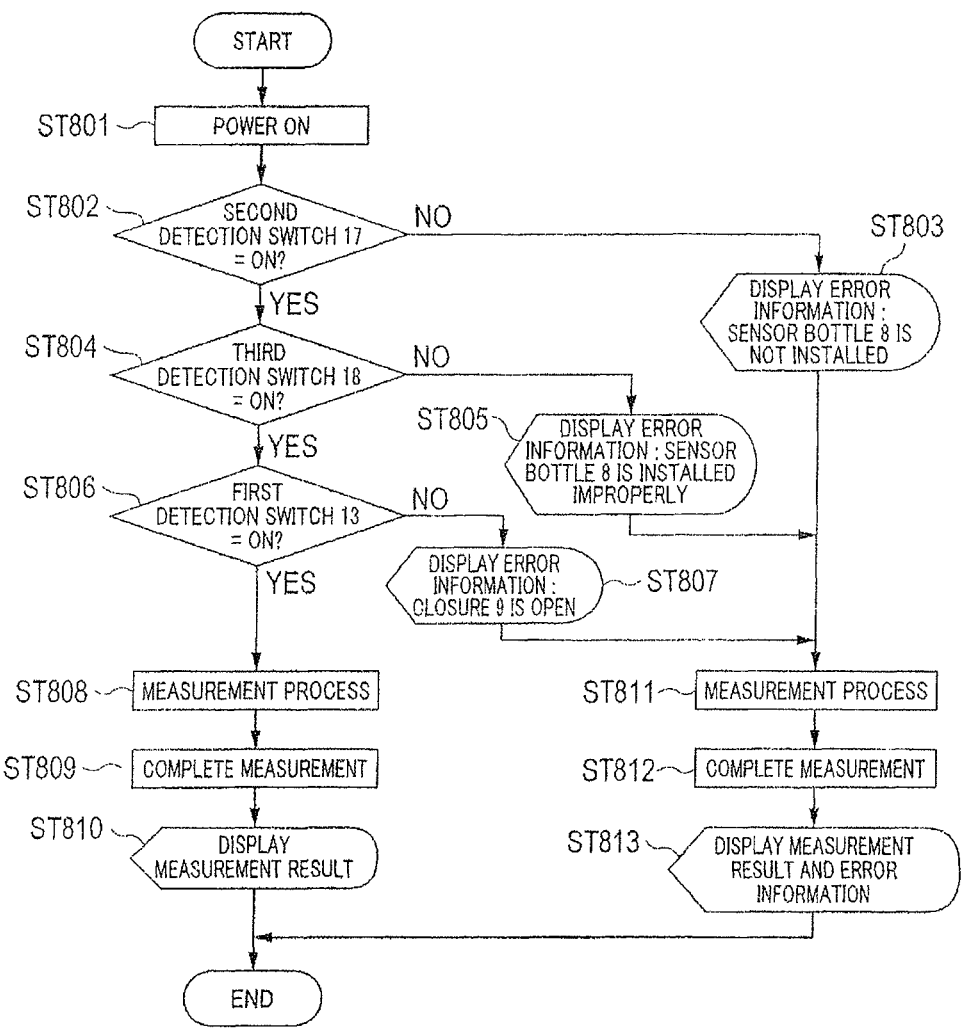
FIG. 9 is a flow chart illustrating a method of acquiring biological information according to Embodiment 1 of the present invention.

A method of acquiring biological information according to Embodiment 1 of the present invention will be described with reference to FIG. 9.

First, a user intending to acquire biological information opens closure 9 of sensor bottle 8. At this time, first detection switch 13 is in OFF state.

Next, the user takes out biological sample measuring sensor 4 from housing section 26 of sensor bottle 8, and then inserts biological sample measuring sensor 4 to sensor installment section 5.

Biological sample measuring sensor 4 is inserted to sensor installment section 5 on the electrode section 40 side.

Next, sensor insertion detection section 20 detects insertion of biological sample measuring sensor 4.

Next, a power of biological sample measuring apparatus 1 is turned ON (step ST801).

Next, control section 19 checks the state of second detection switch 17, and determines whether second detection switch 17 is in ON state (step ST802).

When it is determined that second detection switch 17 is not in ON state (step ST802: NO), control section 19 controls display section 2 to display the fact that sensor bottle 8 is not installed to bottle installment section 6 (step ST803).

When it is determined that second detection switch 17 is in ON state (step ST802: YES), control section 19 checks the state of third detection switch 18 to determine whether third detection switch 18 is in ON state (step ST804).

When it is determined that third detection switch 18 is not in ON state (step ST804: NO), control section 19 controls display section 2 to display the fact that sensor bottle 8 is not properly installed to bottle installment section 6 ("improper sensor bottle mounting") (step ST805).

When it is determined that third detection switch 18 is in ON state (step ST804: YES), control section 19 checks the state of first detection switch 13 to determine whether first detection switch 13 is in ON state (step ST806).

When it is determined that first detection switch 13 is not in ON state (step ST806: NO), control section 19 controls display section 2 to display error information indicating that closure 9 is open (step ST807).

When control section 19 determines that first detection switch 13 is in ON state (step ST806: YES), measurement section 21 does not perform the error information display, but performs a measurement process (step ST808).

Next, the user spots a biological sample on spot application section 41 of biological sample measuring sensor 4 and starts a measurement of the biological sample. At this time, measurement section 21 detects the spot application of the biological sample via electrode section 40 of biological sample measuring sensor 4. Thereafter, measurement section 21 starts the measurement.

Measurement section 21 completes the measurement upon elapse of a predetermined time (for example, about 3 to 15 seconds) after the measurement is started (step ST809).

Then, under the control of control section 19, display section 2 displays only the above-mentioned measurement result measured by measurement section 21 as biological information (step ST810).

Measurement section 21 can perform the measurement process even when first detection switch 13, second detection switch 17 or third detection switch 18 is not in ON state (step ST811). That is, a user can start a measurement of a biological sample by spotting the biological sample on spot application section 41 of biological sample measuring sensor 4. At this time, measurement section 21 detects the spot application of the biological sample via electrode section 40 of biological sample measuring sensor 4. Thereafter, measurement section 21 starts a measurement.

Measurement section 21 completes the measurement upon elapse of a predetermined time (for example, about 3 to 15 seconds) after the measurement is started (step ST812).

Then, display section 2 displays the measurement result as biological information under the control of control section 19, and displays biological information and error information under the control of control section 19 at step ST803, step ST805 or step ST807 (step ST813).

In this case, the measurement result and error information may be simultaneously displayed, may be alternately displayed with large letters, or may be simultaneously displayed while blinking the error information only.

Figure 10:
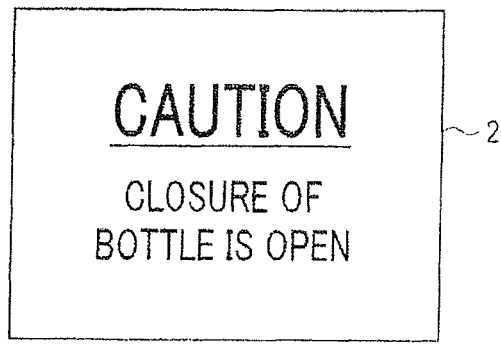
FIG. 10 illustrates an exemplary error display according to Embodiment 1 of the present invention.

When closure 9 is open (step ST807), display section 2 displays letters "CAUTION: CLOSURE OF BOTTLE IS OPEN" as error information as illustrated in FIG. 10, for example.

Effect of Embodiment 1

According to the present embodiment, a user is appropriately notified of the fact that the closure of the housing section that houses the biological sample measuring sensor is open, whereby possible degradation in the performance of the biological sample measuring sensor can be prevented.

Modification of Embodiment 1

In the present embodiment, biological sample measuring apparatus 1 may be provided with a communication section so as to send error information to external apparatuses such as a communication terminal apparatus from the communication section. In addition, at this time, the error information may be sent out in response to a request received from an external apparatus. In this case, a user of the external apparatus at a place distant from biological sample measuring apparatus 1 can recognize that the closure is open.

For example, the communication section of biological sample measuring apparatus 1 in the present embodiment (same as communication section 34 in FIG. 12 described later) sends, to a user's mobile phone or smartphone, a notification about the measurement result and the open/closed state of sensor bottle 8. Thus, the user can promptly take measures such as closing of closure 9 of sensor bottle 8 in response to the received notification.

In addition, in the present embodiment, in the case where the specification of sensor bottle 8 is changed and as a result the sensor bottle cannot be installed to bottle installment section 6 of biological sample measuring apparatus 1, or in an urgent case where a similar sensor of an individually packaged type is used as biological sample measuring sensor 4, it is possible to turn off the detection function of first detection switch 13 which serves as an open/close detection section, and the detection functions of second detection switch 17 and third detection switch 18 which serve as installment detection sections.

In this case, from operation section 3, a user switches "bottle relationship detection function" (switches between ON/OFF) which is one of selective functions in a setting mode, for example. Thus, biological sample measuring apparatus 1 is used as a generally used measuring apparatus having a common measurement function.

Embodiment 2

<Mechanical Configuration of Biological Sample Measuring Apparatus>

A mechanical configuration of biological sample measuring apparatus 30 according to Embodiment 2 of the present invention will be described with reference to FIG. 11. It is to be noted in FIG. 11 that biological sample measuring sensor 4 and sensor bottle 8 are also illustrated together with biological sample measuring apparatus 30.

Figure 11:
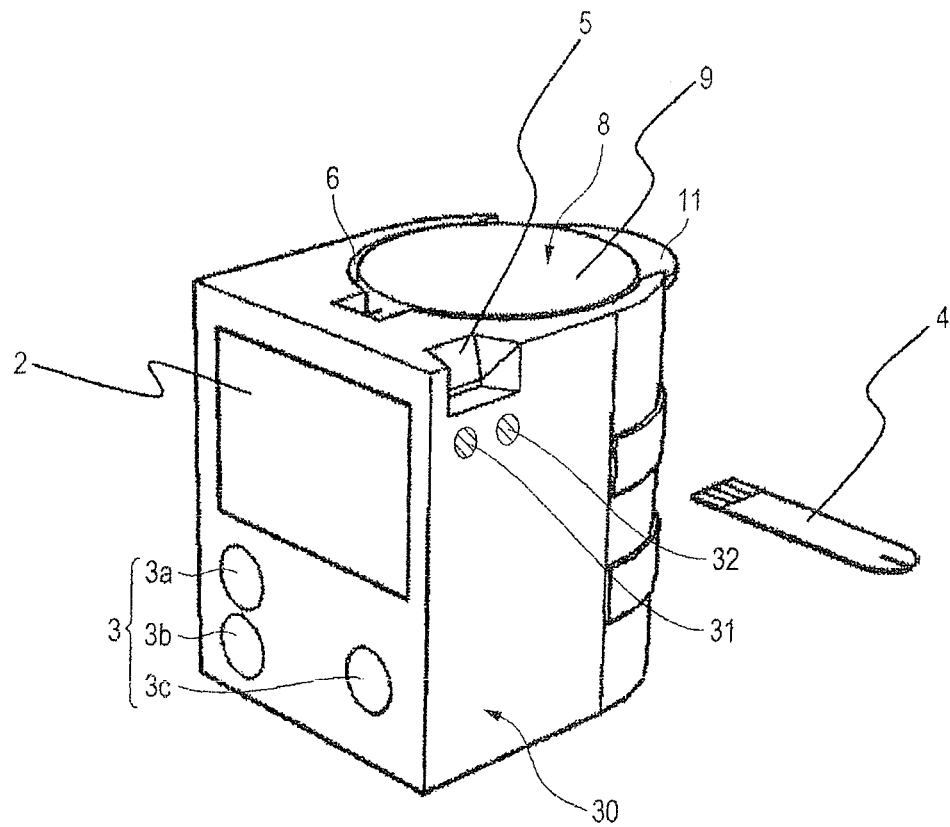
FIG. 11 is a front perspective view of a biological sample measuring apparatus in which a sensor bottle is installed according to Embodiment 2 of the present invention.

In comparison with biological sample measuring apparatus 1 illustrated in FIG. 1 according to Embodiment 1, biological sample measuring apparatus 30 illustrated in FIG. 11 additionally includes temperature measurement section 31 and humidity measurement section 32. It is to be noted that, in FIG. 11, the components having the same configuration as those in FIG. 1 of the above-described Embodiment 1 will be denoted by the same reference numerals, and the descriptions thereof are omitted.

Biological sample measuring apparatus 30 mainly includes display section 2, operation section 3, sensor installment section 5, bottle installment section 6, recess 12, first detection switch 13, second detection switch 17, third detection switch 18, temperature measurement section 31, and humidity measurement section 32. It is to be noted that recess 12, first detection switch 13, second detection switch 17, and third detection switch 18 each have the same configuration as in FIG. 4 although not illustrated in FIG. 11.

Temperature measurement section 31 measures the outside temperature around biological sample measuring apparatus 30. Temperature measurement section 31 is provided in the proximity of sensor installment section 5.

Humidity measurement section 32 measures the outside humidity around biological sample measuring apparatus 30. Similarly to temperature measurement section 31, humidity measurement section 32 is provided in the proximity of sensor installment section 5.

<Electrical Configuration of Biological Sample Measuring Apparatus>

An electrical configuration of biological sample measuring apparatus 30 according to Embodiment 2 of the present invention will be described with reference to FIG. 12.

Figure 8:
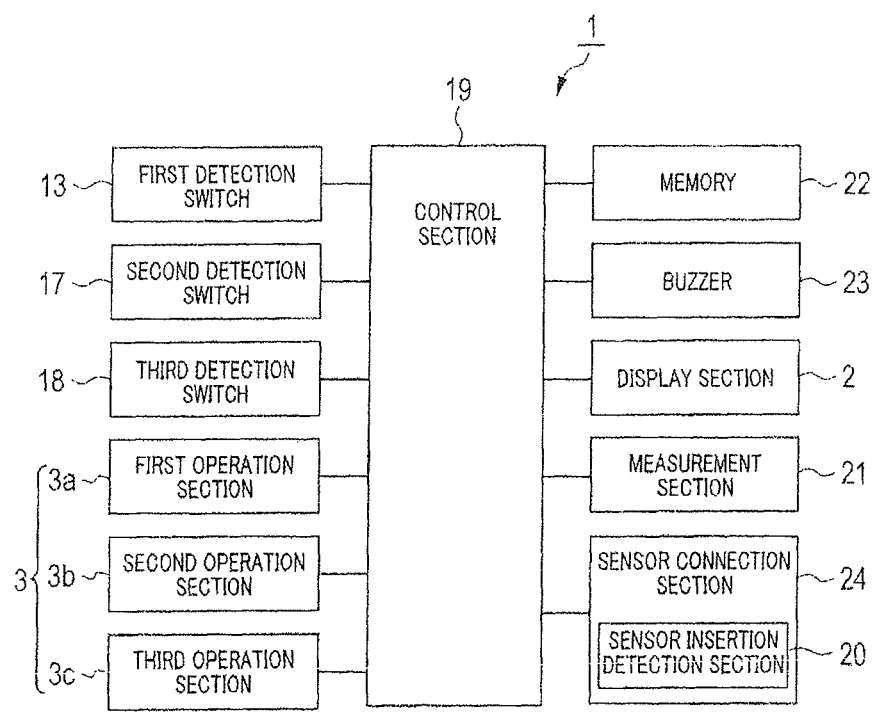
FIG. 8 is a block diagram illustrating a configuration of the biological sample measuring apparatus according to Embodiment 1 of the present invention.
Figure 12:
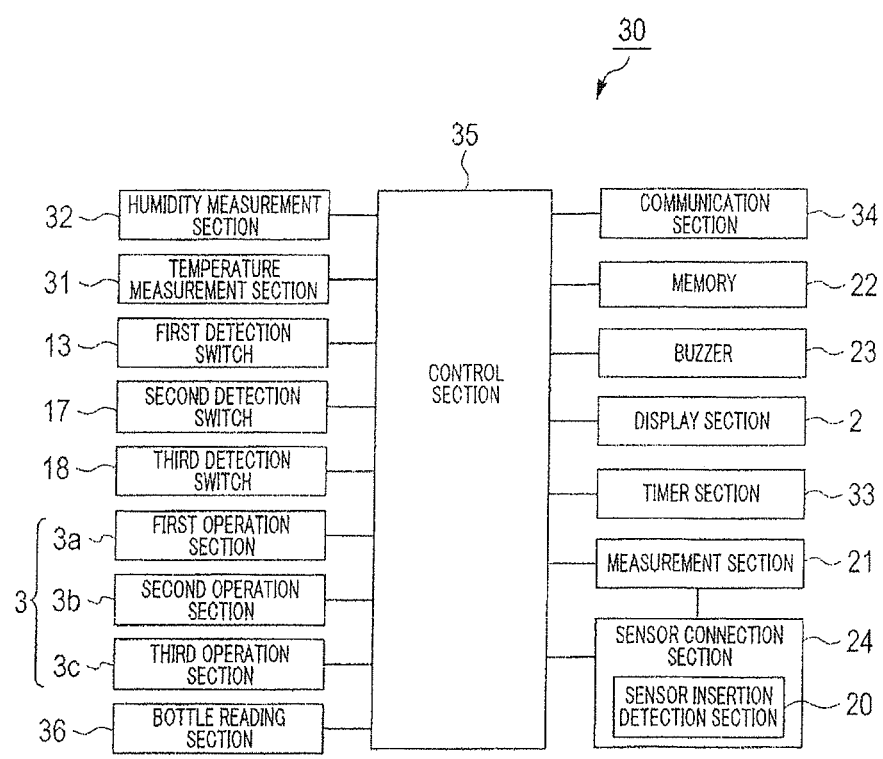
FIG. 12 is a block diagram illustrating a configuration of the biological sample measuring apparatus according to Embodiment 2 of the present invention.

In comparison with biological sample measuring apparatus 1 according to Embodiment 1 illustrated in FIG. 8, biological sample measuring apparatus 30 illustrated in FIG. 12 additionally includes temperature measurement section 31, humidity measurement section 32, timer section 33, communication section 34, and bottle reading section 36. Biological sample measuring apparatus 30 illustrated in FIG. 12 also includes control section 35 in place of control section 19. It is to be noted that, in FIG. 12, the components having the same configuration as those in FIG. 8 will be denoted by the same reference numerals, and the descriptions thereof are omitted.

Biological sample measuring apparatus 30 mainly includes display section 2, first operation section 3a, second operation section 3b, third operation section 3c, first detection switch 13, second detection switch 17, third detection switch 18, sensor insertion detection section 20, measurement section 21, memory 22, buzzer 23, sensor connection section 24, temperature measurement section 31, humidity measurement section 32, timer section 33, communication section 34, control section 35, and bottle reading section 36. It is to be noted that, in FIG. 12, the configurations same as those in FIG. 11 are denoted by the same reference numerals, and the descriptions thereof are omitted.

When timer section 33 detects at first detection switch 13 that closure 9 of sensor bottle 8 is opened, timer section 33 measures a time during which closure 9 of sensor bottle 8 is open (hereinafter referred to as "opening time"). When timer section 33 detects at first detection switch 13 that closure 9 of sensor bottle 8 is closed, timer section 33 outputs information on a measured opening time (the time for which closure 9 has been opened until then) (hereinafter referred to as "opening time information") to control section 35. Control section 35 stores the opening time information received from timer section 33 in memory 22. In addition, control section 35 calculates the accumulation of the opening time, and then stores (updates) also the accumulated opening time information in memory 22. Thereafter, under the control of control section 35, timer section 33 resets the measured opening time.

Under the control of control section 35, communication section 34 sends various kinds of information to external apparatuses. In this case, it is also possible to adopt a configuration in which communication section 34 sends out various kinds of information in response to a request received from external apparatuses. Here, the various kinds of information include opening time information, accumulated opening time information, temperature information measured by temperature measurement section 31, humidity information measured by humidity measurement section 32, and the like. In addition, the opening time information is sent out when the opening time exceeds a predetermined time, or periodically sent out regardless whether the opening time exceeds the predetermined time. In addition, the external apparatuses as the destination of various kinds of information include communication terminal apparatuses such as a personal computer, a mobile phone, and a smartphone, for example.

With the above-mentioned configuration, at a location distant from biological sample measuring apparatus 30, a user having an external apparatus capable of communicating with biological sample measuring apparatus 30 can recognize that closure 9 is in an open state based on the information received from biological sample measuring apparatus 30.

For example, communication section 34 of biological sample measuring apparatus 30 of the present embodiment sends, to a user's personal computer, mobile phone or smartphone, a notification the open/closed state of closure 9 of sensor bottle 8, opening time information, accumulated opening time information, alarm information, and the like, together with a measurement result. Thus, the user can promptly take measures such as closing of closure 9 of sensor bottle 8 in response to the notification.

Control section 35 controls display section 2, first operation section 3a, second operation section 3b, third operation section 3c, and sensor connection section 24. When control section 35 has received a detection result indicating that closure 9 is open from first detection switch 13, control section 35 controls timer section 33 to start a time measurement. In addition, when control section 35 has received a detection result indicating that closure 9 is in a closed state from first detection switch 13, control section 35 controls timer section 33 to stop a time measurement. Thus, control section 35 can cause timer section 33 to measure the opening time. Control section 35 computes an exposure value on the basis of a result of a temperature measurement acquired from temperature measurement section 31, a result of a humidity measurement acquired from humidity measurement section 32, and a result of an opening time measurement acquired from timer section 33. When an exposure value thus calculated is greater than a predetermined value, control section 35 controls display section 2 to display an error message. After controlling display section 2 to display an error message, or when detecting that sensor bottle 8 is newly installed, control section 35 resets timer section 33. Here, the exposure value is a parameter indicating an influence of the outside environment on biological sample measuring sensor 4. It is to be noted that the other configurations of control section 35 than the above-mentioned configurations are the same as those of control section 19, and therefore the descriptions thereof are omitted.

In the above-mentioned configuration, the newly installed sensor bottle 8 can be detected by detecting ON/OFF of second detection switch 17 and third detection switch 18 which serve as the installment detection sections.

Specifically, sensor bottle 8 newly installed to bottle installment section 5 can be detected by detecting that both of second detection switch 17 and third detection switch 18 are again turned into ON state after they are turned into OFF state.

In addition, when sensor bottle 8 is assigned a unique number (serial number or the like), bottle reading section 36 identifies sensor bottle 8 installed to bottle installment section 6 based on the unique number, and outputs the result of identification to control section 35. Thus, biological sample measuring apparatus 30 can detect a newly installed sensor bottle 8. Examples of bottle reading section 36 include a BCR (bar code reader) and the like.

<Method of Determining Display Content and Display Method>

A method of determining display content and a display method according to Embodiment 2 of the present invention will be described with reference to FIG. 13 and FIG. 14.

First, control section 35 determines, at first detection switch 13 serving as the open/close detection section, whether closure 9 of sensor bottle 8 is opened (step ST1201).

When it is determined that closure 9 is in a closed state (step ST1201: NO), control section 35 determines that the measurement of a biological sample is not required, and then the process is terminated.

On the other hand, when control section 35 determines that closure 9 is opened (step ST1201: YES), timer section 33 starts to measure an opening time (step ST1202).

Next, control section 35 determines at sensor insertion detection section 20 whether biological sample measuring sensor 4 is inserted (step ST1203).

When control section 35 determines at sensor insertion detection section 20 that insertion of biological sample measuring sensor 4 is not detected (step ST1203: NO), the process of step ST1203 is repeated, thus waiting for insertion of biological sample measuring sensor 4.

On the other hand, when it is determined at sensor insertion detection section 20 that insertion of biological sample measuring sensor 4 is detected (step ST1203: YES), control section 35 acquires temperature information from temperature measurement section 31, humidity information from humidity measurement section 32, and opening time information from timer section 33 (step ST1204).

After the above-mentioned pieces of information are acquired, control section 35 computes an exposure value based on the pieces of information thus acquired (step ST1205).

Here, control section 35 can obtain an exposure value using the equation "Exposure Value=Exposure Coefficient×Opening Time." To be more specific, control section 35 has an exposure coefficient table of FIG. 14 previously stored in a table. Control section 35 refers to the exposure coefficient table of FIG. 14, and selects an exposure coefficient specified by the temperature acquired from temperature measurement section 31 and the humidity acquired from humidity measurement section 32. Then, using the above-mentioned equation for exposure value, control section 35 multiplies the selected exposure coefficient by the opening time acquired from timer section 33 to calculate an exposure value. Exposure value will be described later.

Control section 35 determines whether a calculated exposure value is greater than a predetermined determination value (step ST1206).

When it is determined that the exposure value is equal to or smaller than a predetermined determination value (step ST1206: NO), control section 35 performs a process for measuring a substrate concentration and the like of the biological sample (step ST1207).

When the measurement process is completed, control section 35 controls display section 2 to display a result of the measurement as biological information (step ST1208), and then the process is terminated.

On the other hand, when it is determined that the exposure value is greater than the predetermined determination value (step ST1206: YES), control section 35 controls display section 2 to display error information.

Then, under the control of control section 35, display section 2 displays the error information (step ST1209), and the process is terminated. At this time, display section 2 can display the error information similarly to the above-mentioned Embodiment 1.

<Exposure Value>

An exposure value calculated by biological sample measuring apparatus 30 according to Embodiment 2 of the present invention will be described with reference to FIG. 14.

Column 141 of FIG. 14 represents ranges of temperature T. Row 142 of FIG. 14 represents ranges of humidity S. On the basis of temperature information measured by temperature measurement section 31 and humidity information measured by humidity measurement section 32, control section 35 finds corresponding exposure coefficient 143. Then, control section 35 performs calculation using exposure coefficient 143 thus found and the opening time measured by timer section 33 to find an exposure value.

In FIG. 14, the higher the temperature T and humidity S, the higher the exposure coefficient. Accordingly, when the exposure coefficient is high, the influence on biological sample measuring sensor 4 is great.

On the other hand, the lower the temperature T and humidity S, the lower the exposure coefficient. Accordingly, when the exposure coefficient is low, the influence on biological sample measuring sensor 4 is small.

In addition, biological sample measuring sensor 4 is more influenced by humidity S than temperature T. Accordingly, comparing the case where humidity S is equal to or 10% (humidity S≤10%) with the case where humidity S is greater than 70% (70%<humidity S) in the same temperature range, the exposure coefficient of the latter case is five times greater than that of the former case. On the other hand, comparing the case where temperature T is equal to or greater than 0° C. and smaller than 10° C. (0° C.≤temperature T≤10° C.), with the case where temperature T is greater than 40° C. (40° C.<temperature T) in the same temperature range, the exposure coefficient of the latter case is two times greater than that of the former case.

In the present embodiment, with the above-mentioned setting of exposure coefficient, the influence of exposure of biological sample measuring sensor 4 can be appropriately determined.

Further, since the exposure value is found by the calculation using the exposure coefficient illustrated in FIG. 14 and the above-mentioned opening time, the longer the opening time, the greater the exposure value. Accordingly, the exposure value indicates that the longer the opening time, the greater the influence on biological sample measuring sensor 4.

It is to be noted that while the exposure coefficients of FIG. 14 are set by temperature T set in a unit of 10° C. and humidity S set in a unit of 20%, this is not limitative as a matter of course. Alternatively, exposure coefficients may be set by temperature T set in a unit of 1° C. to 10° C. and humidity S set in a unit of 2% to 20%.

Effect of Embodiment 2

In the present embodiment, the opening time, temperature and humidity are used to calculate the exposure value, and a notification about the fact that closure 9 of sensor bottle 8 is open is provided on the basis of the calculated exposure value. Thus, according to the present embodiment, in addition to the effect of the above-mentioned Embodiment 1, possible degradation in the performance of the biological sample measuring sensor can be prevented in accordance with the environment in which the biological sample measuring sensor is used.

In addition, according to the present embodiment, the open/closed state of closure 9 of sensor bottle 8, temperature information, humidity information, opening time information, accumulated opening time information, alarm information and the like are sent from the communication section, whereby a user having an apparatus as the destination of the above-mentioned information can recognize that the closure is open at a location distanced from the biological sample measuring apparatus. By receiving the above-mentioned notification about the open/closed state of sensor bottle 8, opening time information, accumulated opening time information, alarm information and the like, a user can promptly take measures such as closing of closure 9 of sensor bottle 8 in response to the notification.

Modification of Embodiment 2

In the present Embodiment, it is possible to issue an alert when a state where the temperature measured by temperature measurement section 31 is equal to or greater than a threshold level is kept for a predetermined time.

In addition, while the exposure value is found using the equation "Exposure Value=Exposure Coefficient×Opening Time" in the present embodiment, error information may be displayed when the accumulated exposure value found by the above-mentioned expression is greater than a determination value.

Figure 13:
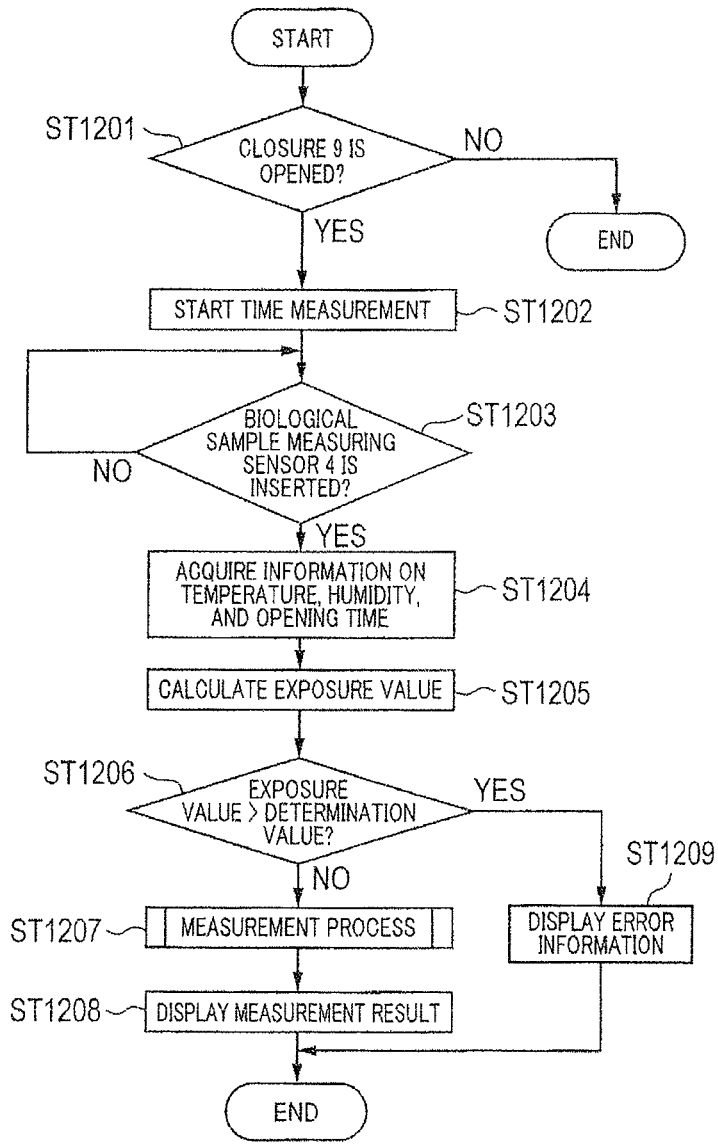
FIG. 13 is a flow chart illustrating a display method according to Embodiment 2 of the present invention.

In this case, in the above-described step ST1205 of FIG. 13, a predetermined accumulation determination value and the accumulation value of the exposure value are compared. In preparation for the case where closure 9 of sensor bottle 8 is repeatedly opened and closed, when first detection switch 13 detects that the state of closure 9 is changed from the open state to the closed state ("open"→"close"), control section 35 accumulates the exposure value found based on the temperature, humidity, and the opening time at this time point.

Figure 15:
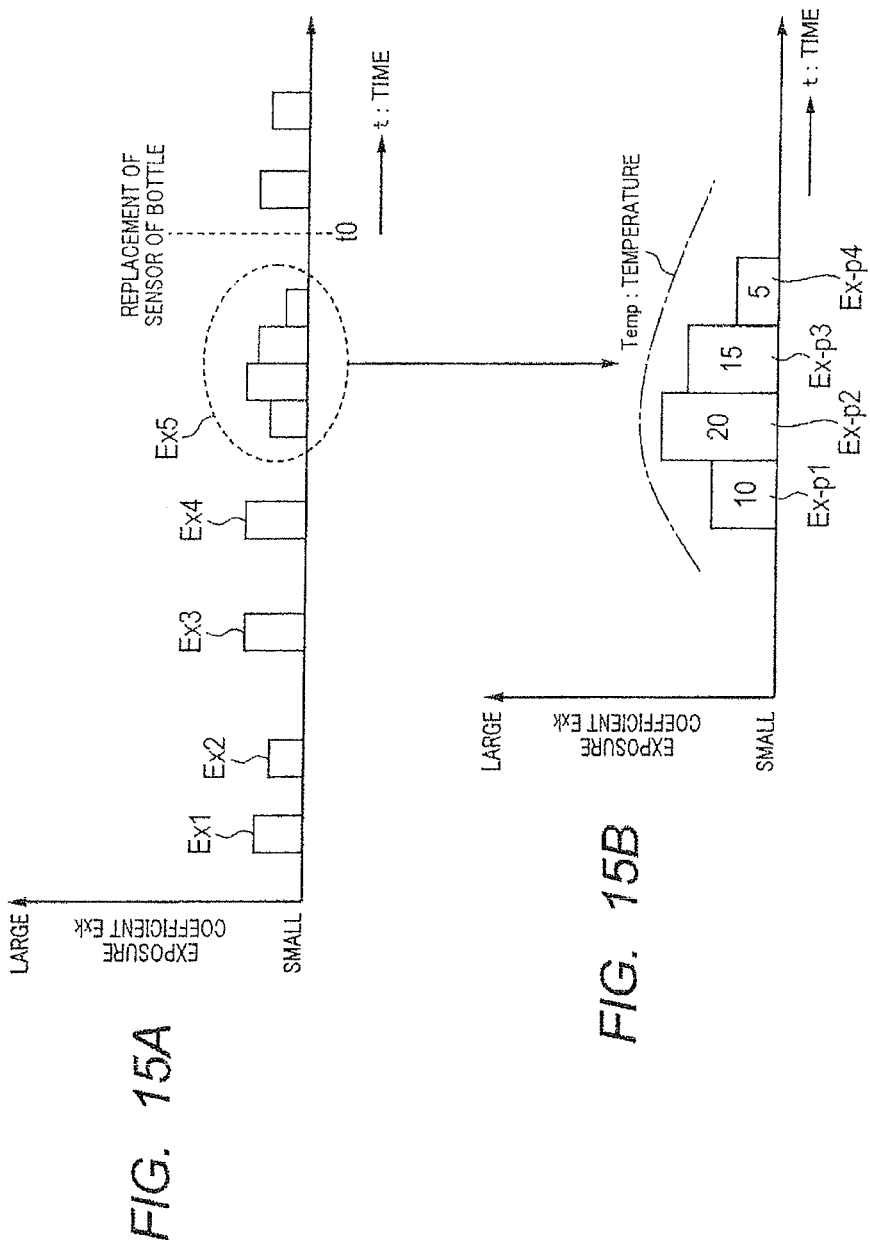
FIGS. 15A and 15B are graphs illustrating exposure values and periodic exposure values according to Embodiment 2 of the present invention.

FIG. 15A illustrates an exemplary case where exposure values are accumulated, wherein the X axis represents time t and the Y axis represents exposure coefficient Exk.

In FIG. 15A, Ex1 to Ex5 represent respective exposure values found when closure 9 is in the "open" state. In this case, the accumulated exposure value is the sum of Ex1 to Ex5 (the accumulated value of exposure values=Ex1+Ex2+Ex3+Ex4+Ex5). It is to be noted that the accumulated value of exposure values is reset when sensor bottle 8 is replaced (=t0).

In addition, in the case where closure 9 of sensor bottle 8 is kept in the open state, it is highly possible that the temperature and humidity change during that time. In this case, control section 35 may periodically (for example, every hour) calculate periodic exposure values by using the temperature measured by temperature measurement section 31 and the humidity measured by humidity measurement section 32. Then, control section 35 may use the sum of the periodic exposure values as an exposure value for the comparison with a predetermined determination value. Thus, biological sample measuring apparatus 30 can obtain an appropriate exposure value corresponding to the change in the surrounding environment.

FIG. 15B illustrates the above-mentioned periodic exposure values. FIG. 15B is an enlarged graph of the exposure value Ex5 of FIG. 15A.

Since temperature T represented by the dashed line in FIG. 15B is changed (the change in humidity S is omitted) while closure 9 is left open, temperature measurement section 31 measures temperature T at certain time intervals (for example, every hour), and humidity measurement section 32 measures humidity S at certain time intervals (for example, every hour). Then, control section 35 finds periodic exposure values Ex-p1 to Ex-p4 by using temperature T and humidity S thus measured at certain time intervals, and takes the sum of the found periodic exposure values as a single exposure value (in this example, Ex5).

Further, in the present embodiment, in the case where the specification of sensor bottle 8 is changed and as a result the sensor bottle cannot be installed to bottle installment section 6 of biological sample measuring apparatus 30, or in an urgent case where a similar sensor of an individually packaged type is used as biological sample measuring sensor 4, it is possible to turn off the detection function of first detection switch 13 which serves as the open/close detection section, and the detection functions of second detection switch 17 and third detection switch 18, which serve as the installment detection sections.

In this case, from operation section 3, a user switches "bottle relationship detection function" (switches between ON/OFF) which is one of selective functions in a setting, mode, for example. Thus, biological sample measuring apparatus 30 is used as a generally used measuring apparatus having only a common measurement function.

Embodiment 3

The configuration of a sensor bottle of the present embodiment is the same as that in FIG. 1 to FIG. 6, and therefore the description thereof is omitted.

<Mechanical Configuration of Biological Sample Measuring Sensor Housing Apparatus>

Figure 16:
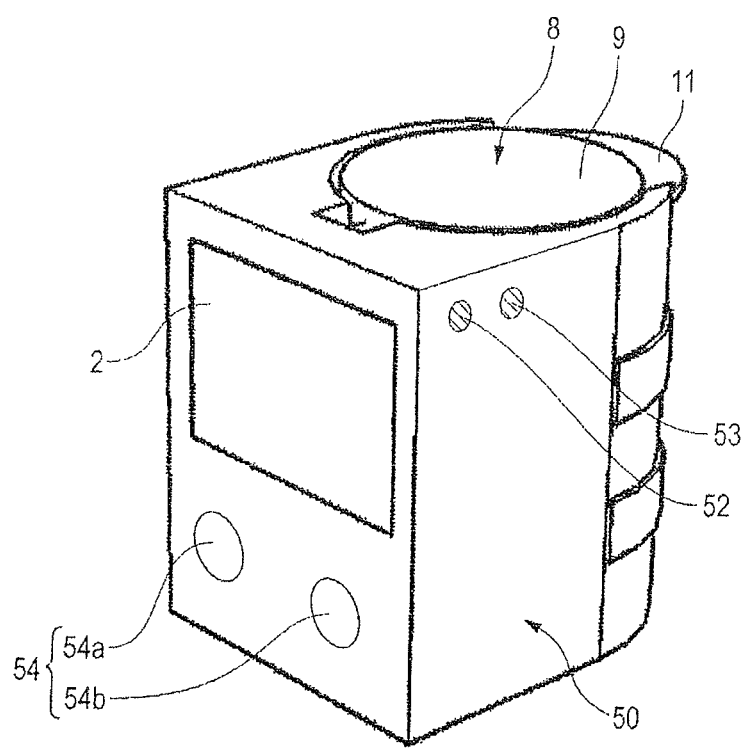
FIG. 16 is a front perspective view of a biological sample measuring sensor housing apparatus in which a sensor bottle is installed according to Embodiment 3 of the present invention.
Figure 17:
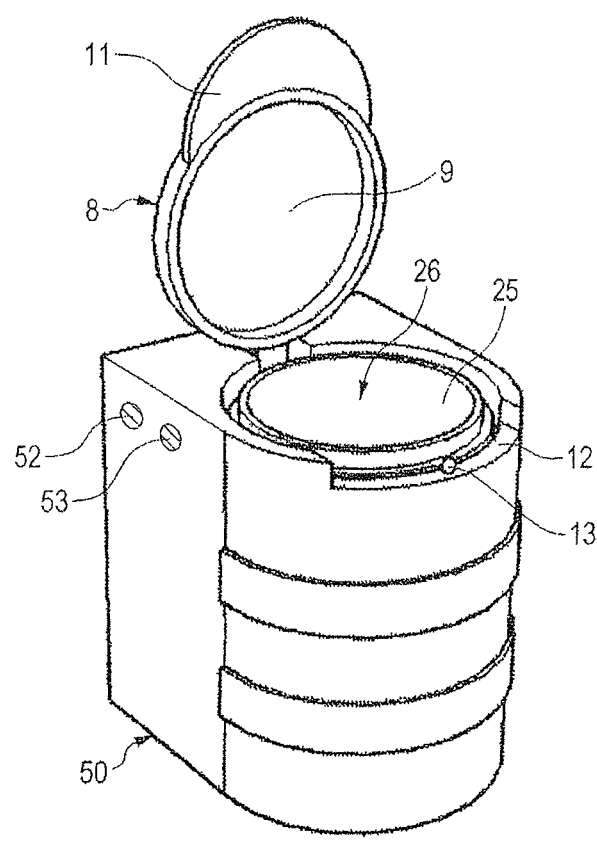
FIG. 17 is a rear perspective view of the biological sample measuring sensor housing apparatus in which the sensor bottle is installed according to Embodiment 3 of the present invention.

A mechanical configuration of biological sample measuring sensor housing apparatus 50 according to Embodiment 3 of the present invention will be described with reference to FIG. 16 and FIG. 17. It is to be noted in FIG. 16 and FIG. 17 that sensor bottle 8 is also illustrated together with biological sample measuring sensor housing apparatus 50.

Biological sample measuring sensor housing apparatus 50 mainly includes display section 2, bottle installment section 6, recess 12, first detection switch 13, second detection switch 17, third detection switch 18, temperature measurement section 52, humidity measurement section 53, and operation section 54. It is to be noted that display section 2, bottle installment section 6, recess 12, first detection switch 13, second detection switch 17, and third detection switch 18 have the same configurations as in the above-mentioned Embodiment 1 (see FIG. 4), and therefore the descriptions thereof are omitted.

Biological sample measuring sensor housing apparatus 50 has a cuboid form.

Display section 2 serving as a notifying section is provided on a front side of biological sample measuring sensor housing apparatus 50. Display section 2 displays error information which indicates that closure 9 is open, and the installment state of sensor bottle 8.

Recess 12 is provided at an upper end portion of the back side of biological sample measuring sensor housing apparatus 50. Recess 12 is provided with first detection switch 13 (see FIG. 17).

Temperature measurement section 52 measures the outside temperature around biological sample measuring sensor housing apparatus 50.

Humidity measurement section 53 measures the outside humidity around biological sample measuring sensor housing apparatus 50.

Operation section 54 includes first operation switch 54a and second operation switch 54b. Operation section 54 is operated to switch a display on display section 2, for example. It is to be noted that the number of operation section 54 is not limited to two.

<Electrical Configuration of Biological Sample Measuring Sensor Housing Apparatus>

Figure 18:
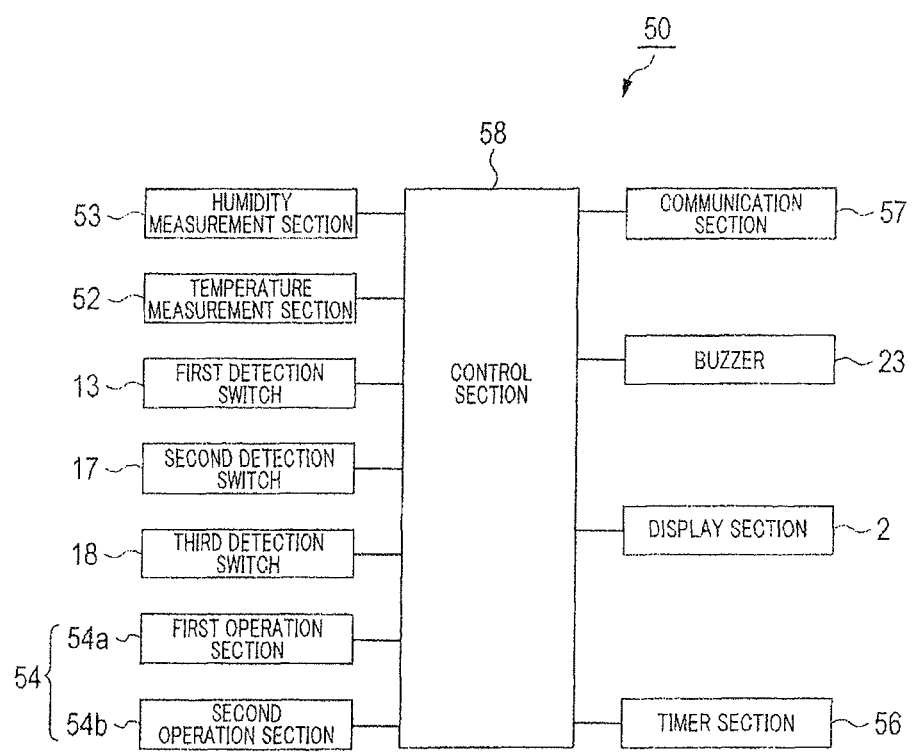
FIG. 18 is a block diagram illustrating a configuration of the biological sample measuring sensor housing apparatus according to Embodiment 3 of the present invention.

An electrical configuration of biological sample measuring sensor housing apparatus 50 according to Embodiment 3 of the present invention will be described with reference to FIG. 18.

Biological sample measuring sensor housing apparatus 50 mainly includes display section 2, first detection switch 13, second detection switch 17, third detection switch 18, buzzer 23, temperature measurement section 52, humidity measurement section 53, first operation section 54a, second operation section 54b, timer section 56, communication section 57, and control section 58. It is to be noted that, in FIG. 18, the configurations same as those in FIG. 16 to FIG. 17 are denoted by the same reference numerals, and the descriptions thereof are omitted.

Timer section 56 measures an opening time, and outputs a measurement result of the opening time to control section 58. Under the control of control section 58, timer section 56 resets the measured opening time.

Under the control of control section 58, communication section 57 sends various kinds of information to external apparatuses. In this case, it is also possible to adopt a configuration in which communication section 57 sends out various kinds of information in response to a request received from external apparatuses. Here, the various kinds of information include opening time information, accumulated opening time information, temperature information measured by temperature measurement section 52, humidity information measured by humidity measurement section 53, and the like. In addition, the opening time information is periodically sent out when the opening time exceeds a predetermined time, or regardless whether the opening time exceeds the predetermined time. In addition, the external apparatuses as the destination of various kinds of information include communication terminal apparatuses such as a personal computer, a mobile phone, and a smartphone, for example.

With the above-mentioned configuration, at a location distant from biological sample measuring sensor housing apparatus 50, a user having an external apparatus capable of communicating with biological sample measuring sensor housing apparatus 50 can recognize that closure 9 is in an open state from the information received from biological sample measuring sensor housing apparatus 50.

For example, communication section 57 of biological sample measuring sensor housing apparatus 50 of the present embodiment sends, to a user's personal computer, mobile phone or smartphone, a notification about the open/closed state of closure 9 of sensor bottle 8, opening time information, accumulated opening time information, alarm information, and the like, together with a measurement result. Thus, the user can promptly take measures such as closing of closure 9 of sensor bottle 8 in response to the notification.

Control section 58 controls first operation section 54a and second operation section 54b. When control section 58 has received a detection result indicating that closure 9 is open from first detection switch 13, control section 58 controls timer section 56 to start a time measurement. In addition, when control section 58 has received a detection result indicating that closure 9 is in a closed state from first detection switch 13, control section 58 controls timer section 56 to stop a time measurement. Thus, control section 58 can cause timer section 56 to measure the opening time. Control section 58 calculates an exposure value on the basis of a measurement result acquired from temperature measurement section 52, a result of a humidity measurement acquired from humidity measurement section 53, and a result of an opening time measurement acquired from timer section 56. When an exposure value thus calculated is greater than a predetermined value, control section 58 controls display section 2 to display an error message. After controlling display section 2 to display an error message, or when detecting that sensor bottle 8 is newly installed, control section 58 resets timer section 56. Unlike control section 19 of the above-mentioned Embodiment 1 and control section 35 of the above-mentioned Embodiment 2, control section 58 has no function of measuring biological samples. It is to be noted that the other configurations of control section 58 than the above-mentioned configurations are the same as those of control section 19, and therefore the description thereof is omitted. In addition, the method for calculating an exposure value is the same as that in the above-mentioned Embodiment 2, and therefore the descriptions thereof are omitted.

In the above-mentioned configuration, the newly installed sensor bottle 8 can be detected by detecting the state (ON/OFF) of second detection switch 17 and third detection switch 18 which serve as the installment detection sections. Specifically, sensor bottle 8 newly installed to bottle installment section 5 can be detected by detecting that both of second detection switch 17 and third detection switch 18 are again turned into ON state after they are turned into OFF state.

<Method of Determining Display Content and Display Method>

Figure 19:
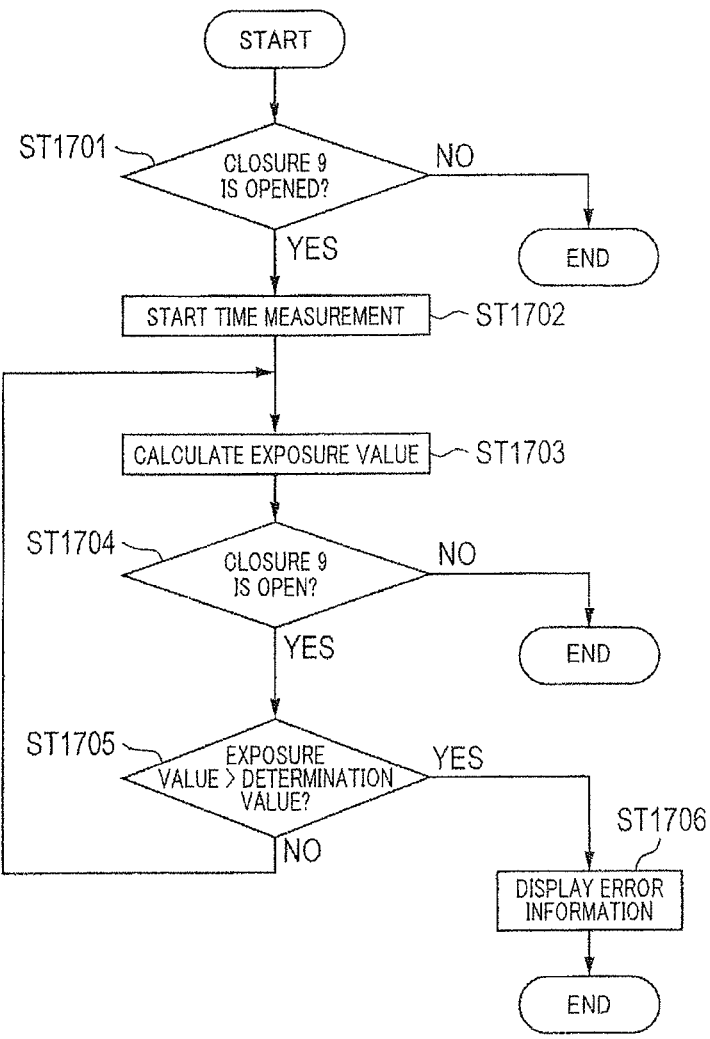
FIG. 19 is a flow chart illustrating a display method according to Embodiment 3 of the present invention.

A method of determining display content and a display method according to Embodiment 3 of the present invention will be described with reference to FIG. 19.

First, control section 58 determines whether closure 9 is opened based on a result detected by first detection switch 13 (step ST1701).

When it is determined that closure 9 is closed (step ST1701: NO), control section 58 terminates the process.

On the other hand, when control section 58 determines that closure 9 is opened (step ST1701: YES), timer section 56 starts to measure an opening time (step ST1702).

Next, control section 58 calculates an exposure value (step ST1703). It is to be noted that the method of finding the exposure value is similar to that in the above-mentioned Embodiment 2. Specifically, an exposure coefficient is found from temperature information and humidity information, and then an exposure value is found by using the found exposure coefficient and the above-mentioned opening time information. Specific description thereof is omitted.

Next, control section 58 determines whether closure 9 is open based on the result detected by first detection switch 13 (step ST1704).

When it is determined that closure 9 is closed (step ST1704: NO), control section 58 terminates the process.

On the other hand, when it is determined that closure 9 is open (step ST1704: YES), control section 58 determines whether the calculated exposure value is greater than a predetermined determination value (step ST1705).

When the exposure value is equal to or smaller than the predetermined determination value (step ST1705: NO), the process is returned to step ST1703 by control section 58.

On the other hand, when it is determined that the exposure value is greater than the determination value (step ST1705: YES), control section 58 controls display section 2 to display error information.

Then, under the control of control section 58, display section 2 displays error information (step ST1706), and the process is terminated. Here, in the above-mentioned procedure of the determination method, the order of step ST1703 and step ST1704 may be reversed since the order makes no practical difference.

Effect of Embodiment 3

In the present embodiment, the opening time, temperature and humidity are used to calculate an exposure value, and based on the exposure value thus calculated, the fact that the closure of the housing section is open is notified. Thus, according to the present embodiment, in addition to the effect of the above-mentioned Embodiment 1, degradation in performance of the biological sample measuring sensor can be prevented in accordance with the environment in which the biological sample measuring sensor is used.

In addition, according to the present embodiment, since biological sample measuring sensor housing apparatus 50 is not provided with the sensor installment section and the measurement section, it is possible to simplify the configuration of the biological sample measuring sensor housing apparatus.

In addition, according to the present embodiment, since the temperature information, humidity information or information on opening time is sent from communication section 57, at a location distant from biological sample measuring sensor housing apparatus 50, a user having an apparatus as the destination of the above-mentioned information can recognize that closure 9 has to be closed.

Modification of Embodiment 3

A modification of Embodiment 3 of the present invention will be described with reference to FIG. 20.

While in the above-mentioned Embodiment 3 the exposure value is found to determine whether to display error information, it is also possible to use the opening time to determine whether to display error information.

Figure 20:
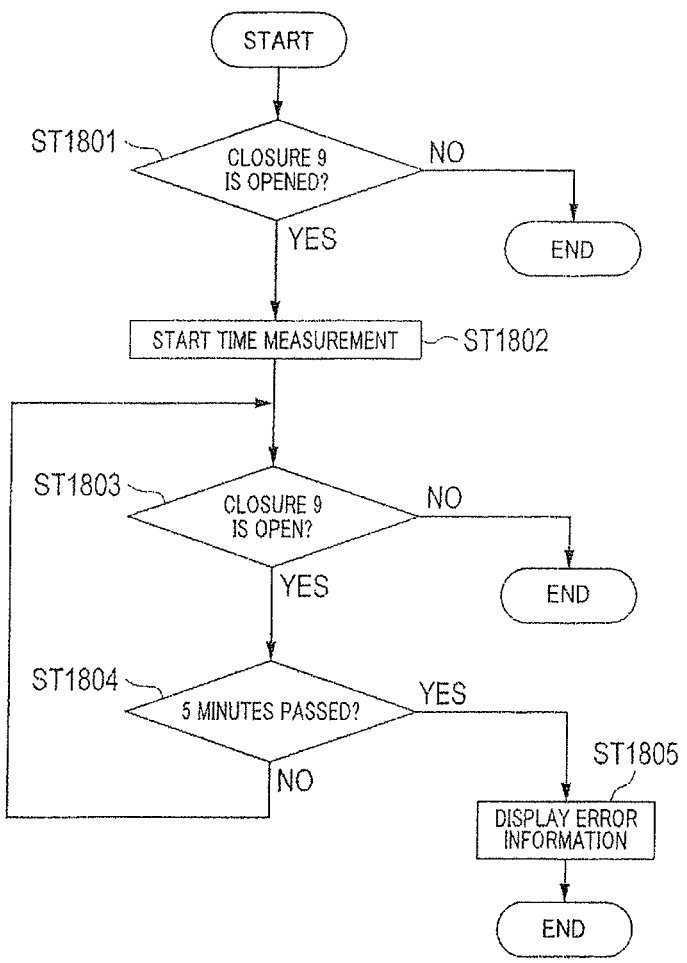
FIG. 20 is a flow chart illustrating a modification of the display method according to Embodiment 3 of the present invention.

To be more specific, referring to FIG. 20, control section 58 first determines whether closure 9 is opened based on a result detected by first detection switch 13 (step ST1801).

When it is determined that closure 9 is closed (step ST1801: NO), control section 58 terminates the process.

On the other hand, when control section 58 determines that closure 9 is opened (step ST1801: YES), timer section 56 starts to measure the opening time (step ST1802).

Next, control section 58 determines whether closure 9 is open based on the result detected by first detection switch 13 (step ST1803).

When it is determined that closure 9 is closed (step ST1803: NO), control section 58 terminates the process.

On the other hand, when it is determined that closure 9 is open (step ST1803: YES), control section 58 determines whether five minutes has passed since the measurement is started at step ST1802 (step ST1804).

When it is determined that the opening time of closure 9 is within five minutes (step ST1803: NO), the process is returned to step ST1803 by control section 58.

On the other hand, when it is determined that the opening time of closure 9 is not within five minutes (step ST1803: YES), control section 58 controls display section 2 to display error information.

Then, under the control of control section 58, display section 2 displays error information (step ST1805), and the process is terminated.

It is to be noted that the display method illustrated in FIG. 20 is applicable not only to the biological sample measuring sensor housing apparatus, but also to the biological sample measuring apparatus of the above-mentioned Embodiments 1 and 2.

In the present embodiment, it is also possible to issue an alert when a state where the temperature measured by temperature measurement section 52 is equal to or greater than a threshold level is kept for a predetermined time.

In the display method illustrated in FIG. 20, display section 2 such as a liquid crystal display is used to display error information, but a display method using LEDs may also be adopted in place of display section 2 of liquid crystal displays or organic EL displays. To be more specific, in place of displaying error information, a method for lighting a red LED and sounding a buzzer alarm may alternatively be adopted. Thus, the configuration of biological sample measuring sensor housing apparatus 50 can be further simplified, reduction in size can be achieved, and the mobility can be improved.

Modification Common to All Embodiments

While the error information is displayed for the notification in the above-mentioned Embodiments 1 to 3, the error information may be notified by other methods such as sound and voice. In this case, for example, the notification may be provided by a buzzer attached to the apparatus. Moreover, in this case, the combination of the display of error information and the buzzer alarm may be used to notify that the closure is open.

In addition, while sensor bottle 8 and biological sample measuring apparatus 1, biological sample measuring apparatus 30, or biological sample measuring sensor housing apparatus 50 are separate components in the above-mentioned Embodiment 1 to Embodiment 3, it is also possible to integrally form sensor bottle 8 and biological sample measuring apparatus 1, biological sample measuring apparatus 30, or biological sample measuring sensor housing apparatus 50.

In addition, while biological sample measuring apparatuses 1 and 30 and biological sample measuring sensor housing apparatus 50 are each provided with first detection switch 13 in the above-mentioned Embodiments 1 to 3, first detection switch 13 may be provided to sensor bottle 8. In this case, even when the installed position of sensor bottle 8 in biological sample measuring apparatus 1, biological sample measuring apparatus 30 or biological sample measuring sensor housing apparatus 50 is somewhat deviated, the open/closed state of closure 9 can be surely detected.

This application is entitled to and claims the benefit of Japanese Patent Application No. 2011-163978 dated Jul. 27, 2011, the disclosure of which including the specification, drawings and abstract is incorporated herein by reference in its entirety.

INDUSTRIAL APPLICABILITY

The biological sample measuring apparatus and the biological sample measuring sensor housing apparatus according to the present invention is suitable for housing a biological sample measuring sensor.

REFERENCE SIGNS LIST 1, 30 Biological sample measuring apparatus
2 Display section
3, 54 Operation section
3a, 54a First operation section
3b, 54b Second operation section
3c Third operation section
4 Biological sample measuring sensor
40 Electrode section
41 Spot application section
5 Sensor installment section
6 Bottle installment section
7, 25 Upper opening portion
8 Sensor bottle
9 Closure
11 Closure opening/closing section
12 Recess
13 First detection switch
17 Second detection switch
18 Third detection switch
19, 35, 58 Control section
20 Sensor insertion detection section
21 Measurement section
22 Memory
23 Buzzer
24 Sensor connection section
31, 52 Temperature measurement section
32, 53 Humidity measurement section
33, 56 Timer section
34, 57 Communication section
36 Bottle reading section
50 Biological sample measuring sensor housing apparatus

The invention claimed is:

1. A biological sample measuring apparatus to which a sensor bottle including a cylindrical housing section and a closure is installed, the housing section having an opening at one end thereof and being capable of housing a biological sample measuring sensor, the closure being configured to open and close the opening, the biological sample measuring apparatus comprising:
a sensor installment section to which the biological sample measuring sensor is installed;
a measurement section that measures biological information by using the biological sample measuring sensor installed to the sensor installment section;
an open/close detection section that detects an open state of the closure; and
a notifying section that notifies a measurement result of the biological information measured by the measurement section, and notifies error information indicating that the closure is open on the basis of a detection result detected by the open/close detection section.

2. The biological sample measuring apparatus according to claim 1, wherein the sensor bottle is installed in a bottomed cylinder having an upper opening portion provided on an upper surface side of the biological sample measuring apparatus.

3. The biological sample measuring apparatus according to claim 2, wherein the open/close detection section is composed of a first detection switch disposed at the upper opening portion.

4. The biological sample measuring apparatus according to claim 3, wherein the closure of the sensor bottle installed to the biological sample measuring apparatus faces a peripheral edge of the upper opening portion when the closure is closed, and
the first detection switch is disposed at the peripheral edge of the upper opening portion.

5. The biological sample measuring apparatus according to claim 1 further comprising an installment detection section that detects whether the sensor bottle is installed, wherein
when the installment detection section detects that the sensor bottle is not installed, the notifying section notifies that the sensor bottle is not installed.

6. The biological sample measuring apparatus according to claim 5, wherein
the sensor bottle is installed in a bottomed cylinder having an upper opening portion provided on an upper surface side of the biological sample measuring apparatus, and
the installment detection section is composed of a bottle detection switch disposed on an internal surface of the bottomed cylinder and/or on a bottom surface of the bottomed cylinder.

7. The biological sample measuring apparatus according to claim 6, wherein the bottle detection switch includes a second detection switch disposed on the internal surface of the bottomed cylinder and a third detection switch disposed on the bottom surface of the bottomed cylinder.

8. The biological sample measuring apparatus according to claim 1, wherein the notifying section provides a notification by displaying the measurement result and the error information, and displays the error information when displaying the measurement result.

9. The biological sample measuring apparatus according to claim 1, wherein the notifying section notifies the error information before notifying the measurement result or after notifying the measurement result.

10. The biological sample measuring apparatus according to claim 1, wherein the notifying section notifies the error information when the open/close detection section detects that the closure is open.

11. The biological sample measuring apparatus according to claim 1, wherein the notifying section displays the error information and sounds a buzzer when notifying the error information.

12. The biological sample measuring apparatus according to claim 1 further comprising:
a temperature measurement section that measures temperature;
a humidity measurement section that measures humidity;
a timer section that measures an opening time during which the closure is open when the open/close detection section detects that the closure is open; and
a control section that calculates an exposure value on the basis of a temperature measured by the temperature measurement section, a humidity measured by the humidity measurement section, and the opening time, the exposure value being a parameter that indicates influence of the outside environment on the biological sample measuring sensor, wherein
the notifying section notifies the error information when the exposure value is equal to or greater than a predetermined value.

13. The biological sample measuring apparatus according to claim 1 further comprising a timer section that measures an opening time during which the closure is open when the open/close detection section detects that the closure is open, wherein the notifying section notifies the error information when the opening time is equal to or longer than a predetermined time.

14. A biological sample measuring sensor housing apparatus to which a sensor bottle including a cylindrical housing section and a closure is installed, the housing section having an opening at one end thereof and being capable of housing a biological sample measuring sensor, the closure being configured to open and close the opening, the biological sample measuring sensor housing apparatus comprising:
- a detection section that detects an open state of the closure; and
- a notifying section that notifies error information indicating that the closure is open on the basis of a detection result detected by the detection section.

* * * * *